United States Patent [19]

Robicsek

[11] 4,444,207
[45] Apr. 24, 1984

[54] METHOD OF ANCHORING A TEMPORARY CARDIAC PACING LEAD

[75] Inventor: Francis Robicsek, Charlotte, N.C.
[73] Assignee: Cordis Corporation, Miami, Fla.
[21] Appl. No.: 312,898
[22] Filed: Oct. 19, 1981
[51] Int. Cl.³ .............................................. A61N 1/02
[52] U.S. Cl. .................................. 128/785; 128/419 P
[58] Field of Search ............................. 128/784–786, 128/419 P, 335, 335.5, 339

[56] References Cited

U.S. PATENT DOCUMENTS 4,010,756  3/1977  DuMont et al. ................. 128/419 P

FOREIGN PATENT DOCUMENTS 2157529  11/1971  Fed. Rep. of Germany ...... 128/335
2846136  10/1978  Fed. Rep. of Germany ... 128/419 P
2438464  10/1978  France ............................... 128/339

Primary Examiner—William E. Kamm
Assistant Examiner—Mitchell J. Shein
Attorney, Agent, or Firm—Henry W. Collins; Thomas R. Vigil

[57] ABSTRACT

A temporary cardiac pacing lead is provided with a multiple stranded flexible wire conductor having an insulating coating extending over a major portion of the length of the wire except for an uninsulated terminal forming portion at each end of the wire conductor. A curved needle is attached to one end of the wire conductor and a straight needle is attached to the other end of the wire conductor. The curved needle is passed through the surface of the wall of the heart and is then drawn back out through the surface of the wall so that a portion of one uninsulated terminal forming portion is embedded in the wall and a portion thereof extends out of the wall of the heart. The needle is then passed through a disk-shaped silastic button. The button is moved frictionally on the wire conductor into contact with the surface of the wall of the heart and the portion of the terminal forming portion extending out of the wall is then severed at a position intermediate the needle and the button. The button serves to retain the wire conductor in a fixed position relative to the wall of the heart during stimulation of the heart.

1 Claim, 3 Drawing Figures

METHOD OF ANCHORING A TEMPORARY CARDIAC PACING LEAD

BACKGROUND OF THE INVENTION

This invention relates to cardiac pacing leads, and more particularly to an improved method for anchoring a temporary pacing lead within the heart.

Temporary leads for use in connecting temporary cardiac pacers to the heart are well known in the medical profession. In general, such leads are constructed of a number of fine stainless steel wires twisted together to form a single, flexible, multiple strand, wire conductor. The major portion of the wire conductor is generally insulated with polyethylene, polytetrafluoroethylene, silicone rubber, nylon or other non-conductive coating. A short length of wire conductor at each end thereof is left uninsulated to provide a terminal forming portion. A curved surgical needle for piercing the heart tissue is mechanically and electrically attached by swaging the needle to one end of the wire conductor. The other end of the wire conductor is attached to a cutting type straight surgical needle for piercing the chest wall from the inside outward so that the wire conductor may be passed through the chest wall and connected to a cardiac pacer. When the temporary lead has been properly positioned, both of the needles are cut off of the ends of the wire conductor. The end of the wire conductor which is then outside of the body, the proximal end, is attached to the cardiac pacer for stimulating the heart. The other end of the wire conductor remains within the heart. A second lead is often used in a similar fashion to complete the circuit, or the return path may be through a stitch of wire in the skin. These prior art temporary leads have a common problem in that when the multiple strand, wire conductor has been passed through a wall of the heart and the needle has been removed, the wire conductor has a tendency to begin to fray or unravel. With the beating of the heart, strands of the wire conductor tend to move relative to the heart thereby preventing satisfactory conduction between the wire conductor and the heart. This causes irritation of the tissue and a rise in the amount of current required for stimulating the heart. In addition, the stranded wires tend to become dislodged from the wall of the heart thereby terminating any further stimulation of the heart.

The present invention contemplates a method of using a novel anchoring device to fix the position of the temporary pacing lead within the heart. In addition, the temporary pacing lead may be intentionally withdrawn from the wall of the heart at a subsequent date from a position external to the body without damage to the heart.

SUMMARY OF THE INVENTION

According to the invention there is provided a temporary pacing lead which includes a multiple strand, flexible wire conductor, a curved needle electrically connected to one end of the wire conductor and a straight needle connected to the other end of the wire conductor. An insulating coating extends over a major portion of the length of the wire conductor except for an uninsulated terminal forming portion at each end of the wire conductor. The curved needle is inserted into a wall of the heart and is drawn back out of the wall so as to embed a portion of one uninsulated terminal forming portion of the wire conductor in the heart while allowing a portion of the terminal forming portion to be drawn out of the wall of the heart. The needle is then passed through a disk-shaped anchoring button and the button is then moved to a position adjacent to the heart. The wire is then severed adjacent the button. The button serves to retain the wire conductor in a fixed position within the heart.

DESCRIPTION OF THE PREFERRED EMBODIMENT

Figure 1:
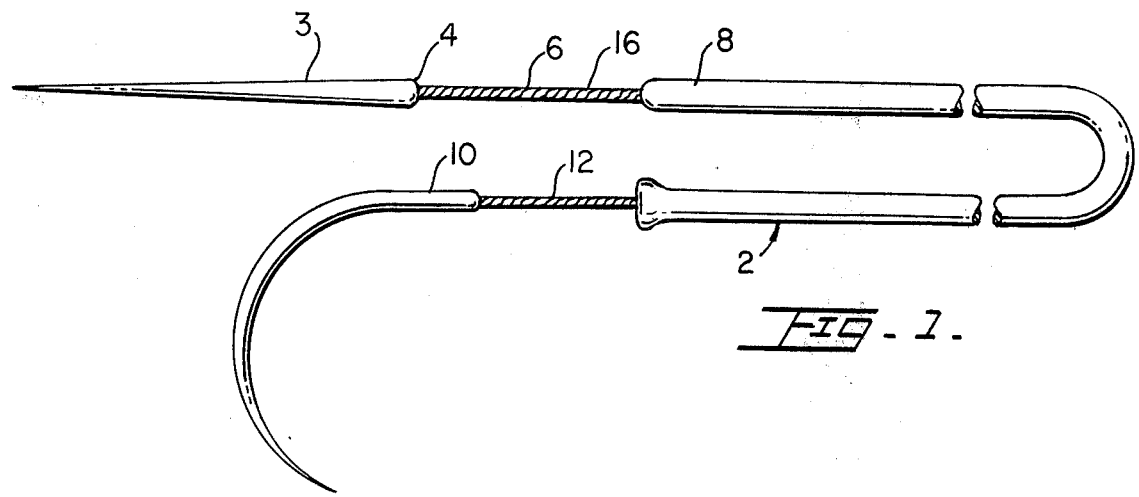
FIG. 1 is an elevational view of a temporary cardiac pacing lead for use with the anchoring method of the present invention.

Referring to FIG. 1 of the drawings, a temporary pacing lead 2 is shown and includes a straight surgical needle 3 having a shank end 4 which is mechanically and electrically attached to a multiple strand, stainless steel wire conductor 6. The shank end 4 of the needle 3 is preferably attached to the wire conductor 6 by swaging.

The wire conductor 6 is coated with insulation 8 over a major portion of the entire length of the wire conductor 6 except for short terminal electrode forming portions 12, 16 at each end of the wire conductor 6.

The other end of the wire conductor 6 is mechanically and electrically attached to a curved surgical needle 10. The shank 11 of the needle 10 is also preferably attached to the wire conductor 6 by swaging.

Figure 2:
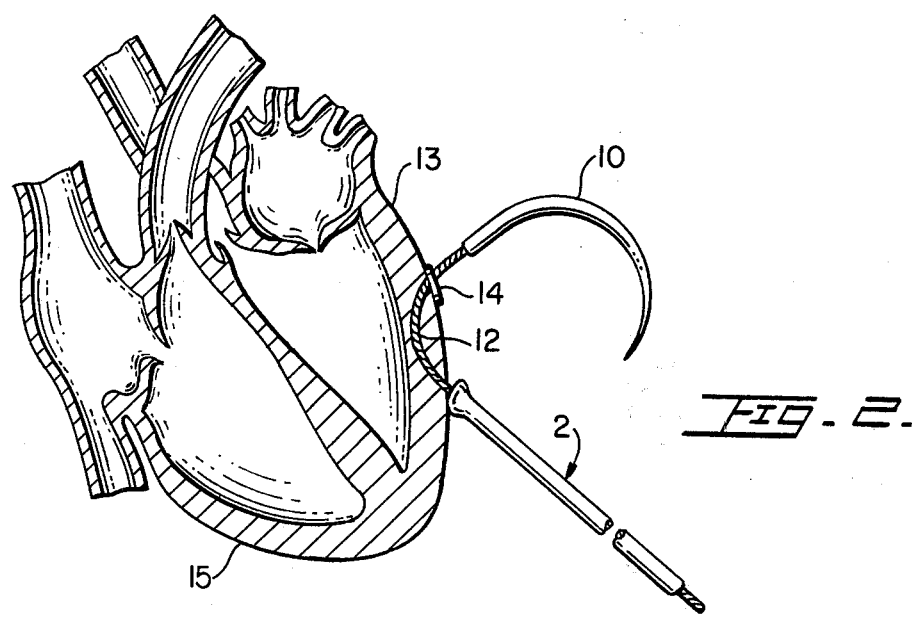
FIG. 2 is a cross-sectional view illustrating a heart with a portion of the temporary pacing lead of FIG. 1 positioned within the wall of the heart.

As shown in FIG. 2, the curved surgical needle 10 is passed into the myocardium 13 of the heart 15. The curved needle 10 is then drawn back out of the myocardium 13 so that the short terminal electrode forming portion 12 is embedded in the myocardium 13. The needle 10 is drawn out of the myocardium 13 a short distance so that the short terminal electrode forming portion 12 also extends out of the surface of the myocardium 13. The curved needle 10 is then passed through a disk-shaped insulative anchor button 14 and the anchor button 14 is moved frictionally down along the needle 10 and along the terminal electrode forming portion 12 of the wire conductor 6 to a position adjacent the surface of the myocardium 13.

Figure 3:
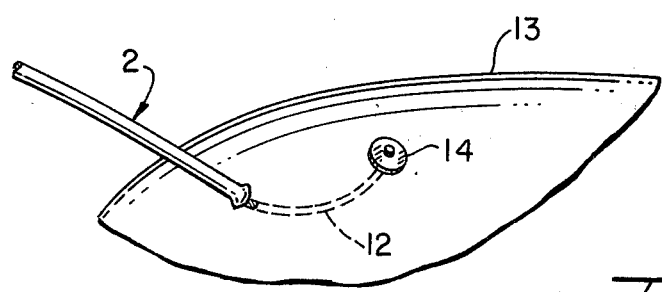
FIG. 3 is a fragmentary perspective view of the lead in a heart wall and shows a button on the distal end of the temporary pacing lead with the curved needle cut away so that the distal end of the temporary pacing lead is fixed in the heart according to the teachings of the present invention.

The anchor button 14 is preferably formed of silicone rubber and is approximately three millimeters in diameter. Once the button 14 is pushed down to the myocardial surface, the terminal electrode forming portion 12 which protrudes from the anchor button 14 is severed at a position adjacent the button 14 as illustrated in FIG. 3. The anchor button 14 serves to fix the position of the multiple strand wire conductor 6 with respect to the myocardium 13 thereby preventing dislodgement of the wire conductor 6 during the beating of the heart 15. On the other hand, when it is desired to withdraw the temporary pacing lead 2 from the heart 15, the terminal electrode forming portion 12 may be withdrawn from the anchor button 14 and from the myocardium 13 by pulling on the proximal end of the wire conductor 6.

The anchor button 14, which is formed of a biologically inert material, remains in the pericardial cavity upon removal of the terminal electrode forming portion 12 of the pacing lead 2 from the heart 15.

Accordingly, the anchor button 14 serves to fix the temporary pacing lead 2 in the wall of the heart 15 while providing an anchoring device which may be detached when it is desired to remove the pacing lead 2 from the heart 15.

Reasonable modifications and variations of the temporary pacing lead are within the scope of the claims which set forth a method of anchoring a temporary pacing lead to the heart.

I claim:

1. A method of temporarily pacing a heart comprising the steps of:

provideing a pacing lead comprising an electrically conductive multiple stranded, flexible wire conductor comprising a twisted strand of wire and having an insulating coating extending over a major portion of the entire length of the wire conductor except for an uninsulated conductive terminal forming portion at each end of the wire conductor, and a needle connected to one of the conductive terminal forming portions;

inserting the needle into the myocardial wall of the heart at a first position on the wall;

passing said needle through a portion of the heart so as to embed a first portion of the conductive terminal forming portion to extend out of the wall of the heart;

passing the needle through an insulative anchor button;

frictionally moving the insulative anchor button over said needle and over said second portion of the conductive terminal forming portion to a position adjacent to the wall of the heart to keep said wire anchored and said twisted strands of said wire from fraying;

severing the second portion of the conductive terminal forming portion at a position adjacent to the insulative anchor button to thereby temporarily fix the position of the conductive terminal forming portion within the heart;

and, when it is desired to withdraw the pacing lead from the heart, pulling on the proximal end of the wire conductor to withdraw same from frictional engagement within the anchor button, said anchor button being allowed to remain within the pericardial cavity with no ill effects to the patient.

* * * * *